(12) United States Patent
Hines et al.

(10) Patent No.: US 8,540,673 B2
(45) Date of Patent: Sep. 24, 2013

(54) DISPOSABLE INFUSION DEVICE WITH ACTUATION LOCK-OUT

(75) Inventors: Craig Hines, San Francisco, CA (US); Cory Williamson, Austin, TX (US)

(73) Assignee: Calibra Medical, Inc., Redwood City, CA (US)

( * ) Notice: Subject to any disclaimer, the term of this patent is extended or adjusted under 35 U.S.C. 154(b) by 934 days.

(21) Appl. No.: 12/077,530

(22) Filed: Mar. 18, 2008

(65) Prior Publication Data

US 2009/0240240 A1 Sep. 24, 2009

(51) Int. Cl.
*A61M 1/00* (2006.01)

(52) U.S. Cl.
USPC ............................................. 604/151

(58) Field of Classification Search
USPC .................... 604/890.1–892.1, 131, 132, 151
See application file for complete search history.

(56) References Cited

U.S. PATENT DOCUMENTS

| | | | |
|---|---|---|---|
| 7,018,361 B2 | 3/2006 | Gillespie, Jr. et al. | |
| 7,250,037 B2 * | 7/2007 | Shermer et al. | 604/134 |
| 2002/0177809 A1 * | 11/2002 | Kriesel et al. | 604/132 |
| 2007/0203454 A1 * | 8/2007 | Shermer et al. | 604/135 |
| 2007/0287960 A1 | 12/2007 | Adams et al. | |
| 2008/0058718 A1 | 3/2008 | Adams et al. | |
| 2008/0097318 A1 | 4/2008 | Adams | |
| 2008/0097324 A1 | 4/2008 | Adams et al. | |
| 2008/0097328 A1 * | 4/2008 | Moberg et al. | 604/155 |
| 2008/0119790 A1 * | 5/2008 | Hawkins et al. | 604/131 |
| 2008/0215015 A1 * | 9/2008 | Cindrich et al. | 604/257 |
| 2009/0088689 A1 | 4/2009 | Carter | |
| 2009/0088694 A1 | 4/2009 | Carter et al. | |

OTHER PUBLICATIONS

International Search Report for PCT Application No. PCT/US2009/037476, dated Jun. 29, 2009 conducted by Korean Intellectual Property Office.

* cited by examiner

*Primary Examiner* — Kevin C Sirmons
*Assistant Examiner* — Imani Hayman
(74) *Attorney, Agent, or Firm* — Wayne C. Jaeschke, Jr.

(57) ABSTRACT

An infusion system includes a wearable infusion device, a safety assembly, and a tool. The device includes a liquid medicament dispenser having a base attachable to a patient's skin and that, when enabled, causes the liquid medicament to flow to beneath the skin of the patient, and an actuator that, when engaged, enables the dispenser. The safety assembly precludes unintended engagement of the actuator and the tool is arranged to disable the safety assembly.

10 Claims, 6 Drawing Sheets

DISPOSABLE INFUSION DEVICE WITH ACTUATION LOCK-OUT

BACKGROUND OF THE INVENTION

The present invention is generally directed to a drug delivery device and more particularly to a disposable infusion device. The present invention is still more particularly directed to such a device capable of delivering any liquid medicament such as, for example, insulin, and which further includes an assembly that precludes unintended dosing the liquid medicament.

Administration of insulin has traditionally been accomplished using a syringe. Recently, needle carrying pen-like devices have also been employed for this purpose. Both forms of insulin administration require the patients to stick themselves each time they inject insulin, often many times a day. Thus, these traditional forms of insulin administration have been a rather pervasive intrusion in the lives and routines of the patient's who have had to adopt and employ them.

More recently, insulin pumps attached by tubing to an infusion set mounted on the patient's skin have been developed as an alternative form of insulin administration. Such pumps may be controlled by a programmable remote electronic system employing short range radio communication between a control device and electronics that control the pump. While such a device may involve fewer needle sticks, it is expensive to manufacture and complex to operate and cumbersome and awkward to wear. The cost of such a device can be many times the daily expense of using a traditional injection means such as a syringe or an insulin pen. It also requires a significant amount of training to use the control device. Great care in programming the device is required because the pump generally carries several days' worth of insulin. Improper programming or otherwise operating the pump can result in an excessive amount of delivered insulin which can be very dangerous and even fatal.

Many patients are reluctant to wear a pump device because it is socially awkward. The user must generally have a noticeable device that is generally as large as a pager attached to the outside of the patients clothes and a catheter like tubing set running from the device to an infusion set located on the patient's body. Besides being obvious and perhaps embarrassing, wearing such a device can be a serious impediment to many activities such as swimming, bathing, athletic activities, and many activities such as sun bathing where portions of the patient's body are necessarily uncovered.

In view of the above, a more cost effective and simple device has finally been proposed whereby an injection system is discreetly attached directly to the skin of the patient. Thus, the device may be attached to the patient under the patient's clothing to deliver insulin into the patient by the manual pumping of small doses of insulin through a temporarily indwelling cannula that is made a part of the pump device. The cannula may be made a part of the drug delivery device before, during or after the attachment of the drug delivery device to the skin of the patient. The device may be made quite small and, when worn under the cloths, entirely unnoticeable in most social situations. It may still carry sufficient insulin to last a patient several days. It can be colored to blend naturally with the patient's skin color so as not to be noticeable when the patient's skin is exposed. As a result, insulin for several days may be carried by the patient discreetly, and conveniently applied in small dosages after only a single needle stick. For a more complete description of devices of this type, reference may be had to co-pending application Ser. No. 11/906,130, filed on Sep. 28, 2007 for DISPOSABLE INFUSION DEVICE WITH DUAL VALVE SYSTEM, which application is owned by the assignee of this application and hereby incorporated herein by reference in its entirety.

The manual pumping mechanism of such a device may be designed to avoid activation by unintentional contact. This may be accomplished, for example, by making it necessary to squeeze two buttons concurrently in different directions so that bumping into a wall, falling down, engaging in contact sports, or other activity of this nature would not accidentally activate the pump. For a more complete description of exemplary devices of this type, reference may be had to co-pending application Ser. No. 11/516,456, filed on Sep. 6, 2006 for DISPOSABLE INFUSION DEVICE WITH LINEAR PERISTALTIC PUMP, which application is owned by the assignee of this application and hereby incorporated herein by reference in its entirety. Further, the pumping mechanism might have at least two trigger type buttons where both a safety button and a pumping button need to be activated concurrently past a trigger point to activate. This safety feature would thus prevent a partial pumping. For a more complete description of such a device of this type, reference may be had to co-pending application Ser. No. 11/906,102, filed on Sep. 28, 2007 for DISPOSABLE INFUSION DEVICE WITH SNAP ACTION ACTUATION, which application is owned by the assignee of this application and hereby incorporated herein by reference in its entirety.

Such a device with such safety features, while appropriate and highly advantageous in most situations, without some locking mechanism that requires intentional intervention by another person such as a supervising adult, might pose a hazard for very young children and for adult patients that need supervision. A drug delivery device of the type described above, especially if loaded with several days supply of insulin, could potentially be dangerous or even life threatening if the child or person needing supervision could inadvertently provide medicament dosage to themselves by unintentionally activating the pump.

Small children are generally very dexterous in their ability to manipulate small mechanical objects. They naturally fidget with and manipulate small objects in their grasp, and would naturally do so with a small device attached to their body. However, the advantage of having the insulin readily available, avoiding multiple needle sticks, and having the infusion of the drug be simple and rapid, are especially important with such patients. Functionality associated with such a device preventing unintentional dosing activation without supervisory involvement would be highly desirable.

Likewise, where an adult, such as a mentally confused patient, requires the supervision of another person, such a mechanism may be important. Diabetes is more prevalent as age increases, and thus will impact many patients suffering from Alzheimer disease or dementia due to advanced age. Likewise, mental impairment is one of the unfortunate side effects that may accompany a prolonged struggle with the diabetic condition. Although mentally confused, such a patient might none the less be fully capable of the physical dexterity needed to accidentally or unintentionally operate the drug delivery device, and might not even be aware that they had done so. As is the case with very small children, such an activation of the drug delivery device could well be dangerous.

Hence, there is a need in the art for a wearable drug delivery device that includes means for precluding or preventing unintended dosing actuation of the device. Preferably, such a mechanism would securely lock the drug delivery device and require a person other than the patient, such as an adult or caretaker, to unlock and activate the device. Permitting such action by the other person easily and reliably would also be highly desirable. This present invention addresses these and other issues.

SUMMARY OF THE INVENTION

In one embodiment, a wearable infusion device comprises a liquid medicament dispenser having an enclosure and a base attachable to a patient's skin and that, when enabled, causes the liquid medicament to flow to beneath the skin of the patient, an actuator that, when engaged, activates the dispenser, and a safety assembly that precludes unintended engagement of the actuator.

The safety assembly may be arranged to preclude access to the actuator. The actuator may comprise at least one control button which, when depressed, causes engagement of the actuator and the safety assembly may comprise a moveable cover overlying the at least one control button.

The safety assembly may further comprise a lockable lock mechanism that precludes movement of the moveable cover unless the lock mechanism is unlocked. The safety assembly may include a frame attachable to the enclosure of the device and the frame may carry the moveable cover. The moveable cover may be mounted for sliding movement on the frame.

The actuator may comprise a pair of opposed actuator buttons which, when concurrently pressed, cause engagement of the actuator and the safety assembly may comprise a cover overlying only one of the control buttons. The safety assembly may further include an activation lever and a drive member. The drive member may be arranged to cause the activation lever to depress the only one of the control members. The cover may overlie the activation lever and the activation lever may be arranged to engage the only one of the control members beneath the cover.

The safety assembly may be arranged to disable actuator engagement. The actuator may comprise at least one control button which, when depressed, causes engagement of the actuator and the safety assembly may be arranged to preclude depression of the at least one control button.

The safety assembly may further include a locking pin arranged to interfere with the depression of the at least one control button. The safety assembly may further include an urging member that urges the locking pin into an interfering position to interfere with the depression of the at least one control button. The locking pin may further be arranged for temporary release from the interfering position against the urging of the urging member.

The safety assembly may be arranged to attach to the enclosure. The actuator may comprise at least one control button which, when depressed, causes engagement of the actuator and the safety assembly may be arranged to preclude depression of the at least one control button.

The safety assembly may include a sliding member arranged to slide along the enclosure between a first position blocking depression of the at least one control button to a second position clear of the control button.

In another embodiment, an infusion system comprises a wearable infusion device including a liquid medicament dispenser having a base attachable to a patient's skin and that, when enabled, causes the liquid medicament to flow to beneath the skin of the patient, an actuator that, when engaged, enables the dispenser, and a safety assembly that precludes unintended engagement of the actuator. The system further comprises a tool that disables the safety assembly.

The safety assembly may be arranged to preclude access to the actuator. Alternatively, the safety assembly may be arranged to disable actuator engagement.

BRIEF DESCRIPTION OF THE DRAWINGS

The features of the present invention which are believed to be novel are set forth with particularity in the appended claims. The invention, together with further features and advantages thereof, may best be understood by making reference to the following description taken in conjunction with the accompanying drawings, in the several figures of which like reference numerals identify identical elements, and wherein:

DETAILED DESCRIPTION OF THE INVENTION

Figure 1:
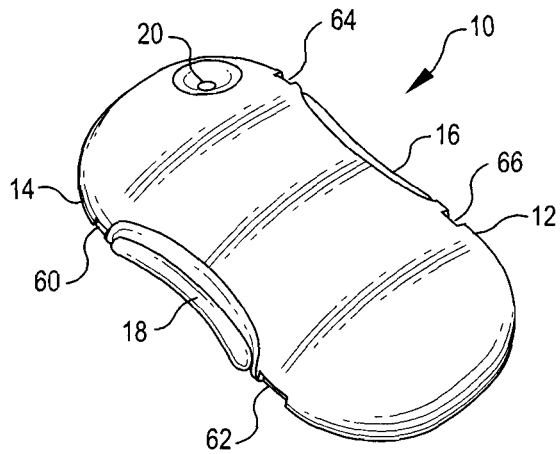
FIG. 1 is a perspective view of a first infusion device embodying certain aspects of the present invention.

Referring now to FIG. 1 it is a perspective view of a first infusion device embodying certain aspects of the present invention. The device 10 generally includes an enclosure 12, a base 14, a first actuator control button 16, and a second actuator control button 18.

The base 14 preferably includes an adhesive coating to permit the device to be adhered to a patient's skin. The adhesive coating may originally be covered with a releasable cover that may be pealed off of the base 14 when the patient endeavors to deploy the device 10.

The device 10 may be mated with a previously deployed cannula assembly. However, it is contemplated herein that the various aspects of the present invention may be realized within a device that may be alternatively first adhered to the patient's skin followed by the deployment of a cannula thereafter. The device 10 further includes a fill port 20 to enable the device reservoir to be filled after deployment and prior to its first use.

The actuator buttons 16 and 18 are placed on opposites sides of the device 10 and directly across from each other. This renders more convenient the concurrent depression of the buttons when the patient wishes to receive a dose of the liquid medicament contained within the device 10. This arrangement also imposes substantially equal and opposite forces on the device during dosage delivery to prevent the device from being displaced and possibly stripped from the patient. The actuator button 16 may serve as a valve control which, when in a first position, establishes a first fluid path between the device reservoir and the device pump to support pump filling, and then, when in a second or depressed position, establishes a second fluid path between the device pump and the device outlet or cannula to permit dosage delivery to the patient. A linkage between the control actuator buttons 16 and 18 permits actuation of the device pump with the actuator control button 18 only when the second fluid path has been established by the first actuator control button 16. Hence, the first actuator control button 16 may be considered a safety control.

Figure 2:
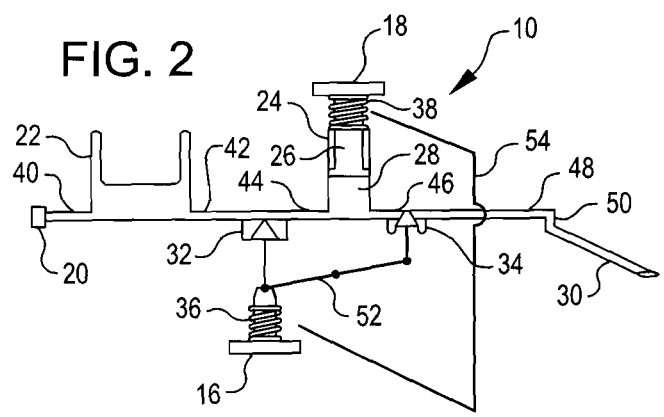
FIG. 2 is a schematic representation of the valves and pump of the device of FIG. 1.

Referring now to FIG. 2, it is a schematic representation of the valves and pump of the device 10 of FIG. 1. The operative elements shown in FIG. 2 may also be employed to advantage in each of the device embodiments disclosed herein. As may be seen in FIG. 2, the device 10 further includes the fill port 20, a reservoir 22, a pump 24, and the cannula 30. The device further includes a first valve 32 and a second valve 34. Fluid conduit 40 provides a fluid connection between the fill port 20 and the reservoir 22, fluid conduit 42 provides a fluid connection between the reservoir 22 and the first valve 32, fluid conduit 44 provides a fluid connection between the first valve 32 and the pump 24, fluid conduit 46 provides a fluid connection between the pump 24 and the second valve 34, and fluid conduit 48 provides a fluid connection between the second valve 34 and the device outlet 50. The outlet 50 is arranged to communicate with the cannula 30.

It may also be noted that the actuator buttons 16 and 18 are spring loaded by springs 36 and 38. The springs are provided for returning the actuator buttons to the first position after a dosage is administered.

The pump 24 of the device 10 comprises a piston pump. The pump 24 includes a pump piston 26 and a pump chamber 28. In accordance with this embodiment, the actuator control button 18 is directly coupled to and is an extension of the pump piston 26.

With further reference to FIG. 2, the device additionally includes a first linkage 52 and a second linkage 54. The first linkage is a toggle linkage between the first valve 32 and the second valve 34. It is arranged to assure that the second valve 34 does not open until after the first valve 32 is closed. The second linkage 54 is between the first actuator button 16 and the second actuator button 18. It is arranged to assure that the pump does not pump until after the first valve is closed and the second valve is opened by the first actuator button 16.

Still further, the second valve 34 is a safety valve that closes tighter responsive to increased fluid pressure within fluid conduit 46. This assures that the liquid medicament is not accidentally administered to the patient notwithstanding the inadvertent application of pressure to the reservoir, for example. In applications such as this, it is not uncommon for the reservoir to be formed of flexible material. While this has its advantages, it does present the risk that the reservoir may be accidentally squeezed as it is worn. Because the second valve only closes tighter under such conditions, it is assured that increased accidental reservoir pressure will not cause the fluid medicament to flow to the cannula.

In operation, the reservoir is first filled through the fill port 20 to a desired level of medicament. In this state, the valves 32 and 34 will be as shown. The first valve 32 will be open and the second valve 34 will be closed. This permits the piston chamber 28 to be filled after the reservoir is filled. The cannula 30 may then be deployed followed by the deployment of the device 10. In this state, the valves 32 and 34 will still be as shown. The first valve 32 will be open and the second valve 34 will be closed. This permits the pump chamber 28 to be filled through a first fluid path including conduits 42 and 44 as the piston 24 returns to its first position after each applied dose.

When the patient wishes to receive a dose of medicament, the actuator buttons are concurrently pressed. In accordance with aspects of the present invention, the linkage 52 causes the first valve 32 to close and the second valve 34 to thereafter open. Meanwhile, the second linkage 54 precludes actuation of the pump 24 until the first valve 32 is closed and the second valve 34 is opened by the first actuator button 16. At this point a second fluid path is established from the pump 24 to the cannula 30 through fluid conduits 46 and 48 and the outlet 50. The medicament is then administered to the patient through cannula 30.

Once the medication dosage is administered, the piston 24, and thus the actuator button 18, is returned under the spring pressure of spring 38 to its initial position. During the travel of the piston back to its first position, a given volume of the liquid medicament for the next dosage delivery is drawn from the reservoir into the pump chamber 28 to ready the device for its next dosage delivery. For a more complete description of the internal mechanism of the device 10 resulting in the operation described above, reference may be had to the aforementioned co-pending application Ser. No. 11/906,130, filed on Sep. 28, 2007 for DISPOSABLE INFUSION DEVICE WITH DUAL VALVE SYSTEM.

Referring again to FIG. 1, it may be noted that the device 10 further includes a pair of notches including notch 60 on one side of actuator button 18 and another notch 62 on the opposite side of the actuator button 18. The device also includes another pair of notches including notch 64 on one side of actuator button 16 and another notch 66 on the opposite side of actuator button 16. As will be seen subsequently, the notches may be used to support the attachment of a safety assembly on the device 10. The safety assembly is operable to preclude unintended actuation engagement of the actuator buttons 16 and 18.

Figure 3:
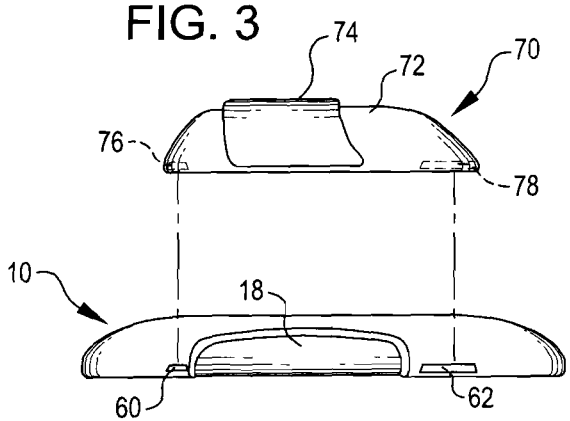
FIG. 3 is an exploded side view of the device of FIG. 1 and a safety assembly embodying aspects of the present invention.
Figure 4:
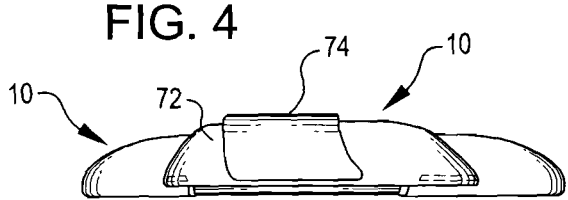
FIG. 4 is a side view of the device and safety assembly of FIG. 3 joined together according to certain aspects of the present invention.

FIG. 3 shows the safety assembly 70 before attachment to the device 10. The safety assembly 70 generally includes a frame 72 and a moveable cover 74. To enable attachment of the assembly 70 to the device 10, the frame 72 of the assembly 70 may be provided with a first pair of tabs 76 and 78 which correspond to and are received by the notches 60 and 62 respectively, and a second pair of notches (not shown) which correspond to and are received by the notches 64 and 66. In this manner, the frame 72 may be snap fitted to the device 10. As may be seen in FIG. 4, when the assembly 70 is received on the device 10, the moveable cover 74 precludes access to the actuator buttons 16 and 18.

Figure 5:
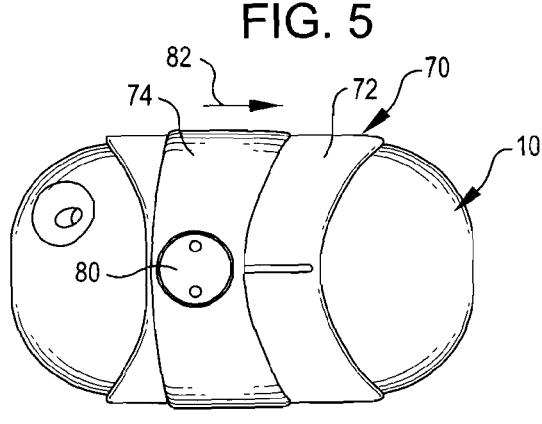
FIG. 5 is a top view of the device and safety assembly of FIG. 4 showing the safety assembly precluding access to the actuator of the device.
Figure 6:
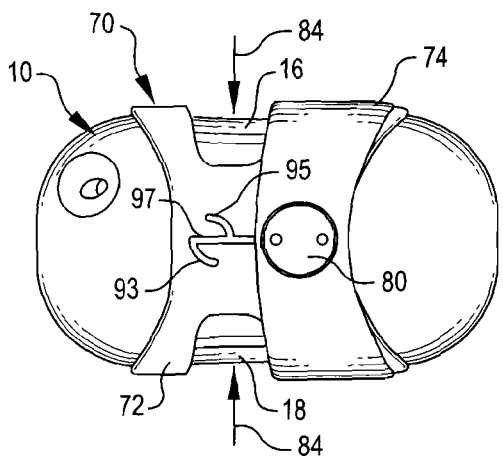
FIG. 6 is a top view of the device and safety assembly of FIG. 4 showing a moveable cover of the safety assembly unlocked and slid longitudinally to permit access to the actuator of the device.

As may be seen in the top view of FIG. 5, the assembly 70 further includes a lock 80 carried by the cover 74. A key, to be described subsequently, is used to unlock the lock 80. When the lock 80 is unlocked, the moveable cover is free to be slid back as indicated by the arrow 82, exposing the actuator buttons 16 and 18 as may be seen in FIG. 6. The actuator buttons 16 and 81 may now be concurrently depressed as indicated by arrows 84 to permit actuating engagement of the actuator buttons 16 and 18 and an intended delivery of an insulin bolus dosage to the patient.

Figure 7:
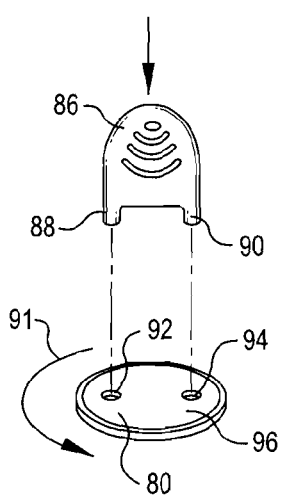
FIG. 7 is a perspective view, to an enlarged scale, of the lock and key of the safety assembly of FIGS. 3-6.

FIG. 7 shows the lock 80 and its corresponding key 86 in greater detail. The key 86 includes a pair of extensions 88 and 90 which may be received in a corresponding pair of indentations 92 and 94. Extending beneath the base 96 of the lock 80 from the indentions 92 and 94 are a pair of integral pins (not shown). When the lock 80 is locked, a first pin resides in a first track 93 of the frame 72 and the other pin resides in a second track 95. This precludes sliding movement of the cover 74. However, when the key 86 turns the lock base 96 as indicated by arrow 91, the pins enter a common track 97 in aligned relation permitting the cover 74 to slide back to the position shown in FIG. 6. This uncovers the actuator buttons 16 and 18 permitting actuation thereof. When the bolus of insulin is delivered, a reverse procedure may be followed to return the cover 74 to its original position covering the actuator buttons 16 and 18 and permitting the lock base 96 to be turned back by the key 86 to a locked condition.

Figure 8:
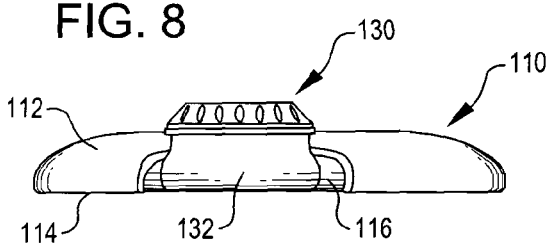
FIG. 8 is a side view of another infusion device and joined safety assembly according to further aspects of the present invention.
Figure 9:
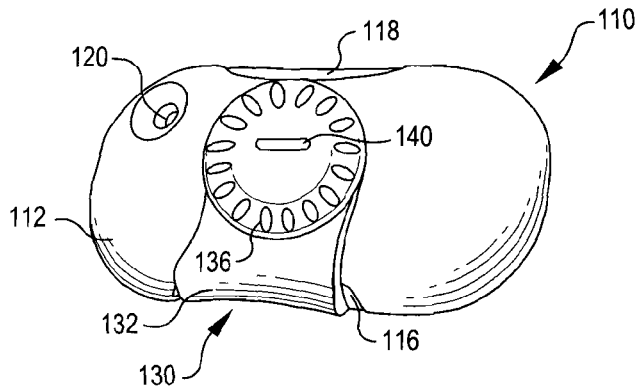
FIG. 9 is a top view of the infusion device and joined safety assembly of FIG. 8.
Figure 10:
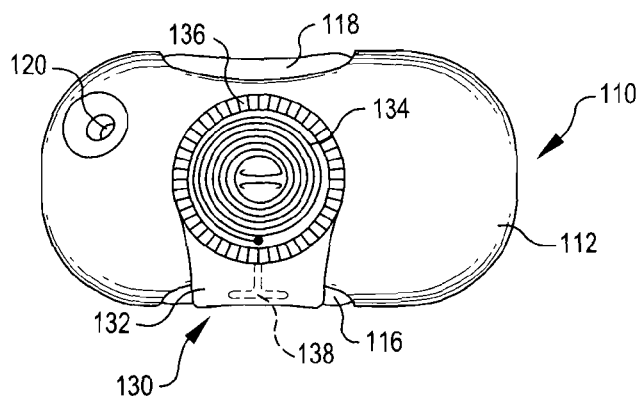
FIG. 10 is a top view of the infusion device and joined safety assembly of FIG. 8 illustrating an energy storage element therein to enable self-powered actuation of the infusion device.

Referring now to FIGS. 8-10, they illustrate another device 110 and safety assembly 130 according to a further embodiment of the present invention. The device 110 generally includes an enclosure 112, a base 114, a first actuator button 116, a second actuator button 118, and a fill port 120.

As in the previous embodiment, the base 114 preferably includes an adhesive coating to permit the device to be adhered to a patient's skin. The adhesive coating may originally be covered with a releasable cover that may be pealed off of the base 114 when the patient endeavors to deploy the device 110.

Also as in the previous embodiment, the device 110 may be mated with a previously deployed cannula assembly or alternatively first adhered to the patient's skin followed by the deployment of a cannula thereafter. The fill port 120 enables the device reservoir to be filled after deployment and prior to its first use.

Again, the actuator buttons 116 and 118 are placed on opposites sides of the device 110 for convenient concurrent depression of the buttons when the patient wishes to receive a dose of insulin. The actuator button 116 may serve as a valve control which, when actuated, establishes' a fluid path between the device pump and the device outlet or cannula to permit dosage delivery to the patient. The linkage 54 (FIG. 2) between the control actuator buttons 116 and 118 permits actuation of the device pump with the actuator control button 118 only when the fluid path between the device pump and the device outlet or cannula has been established by the first actuator control button 116.

The safety assembly 130 is preferably arranged to snap onto the enclosure 112 of the device 110. The safety assembly 130 includes a cover 132 that overlies and precludes access to only actuator button 116 of the actuator buttons 116 and 118.

As may be best seen in FIG. 10, the safety assembly 130 further includes a drive member in the form of a coiled spring 134, and ratchet knob 136 for winding the spring 134 and an activation lever 138. The activation lever 138 lies under the cover 132 and engagingly over the actuator button 116. The lever 138 is coupled to and driven by the spring 134. When activated, the lever 138 depresses the actuator button 116 under power by the spring 134. When the lever 138 is thus activated, the actuator button 116 is depressed and held in that state, conditioning the actuator button 118 for actuation by virtue of the linkage 54 (FIG. 2). Now, the device 110 may be actuated to deliver a dose of insulin upon the depressing of actuator button 118.

A lock having a key slot 140 may be employed to control activation of the lever 138. To that end, to activate the lever, a key (not shown) may be inserted into the key slot 140 and turned, for example. Alternatively, the safety assembly 132 may include a timer for conditioning the device for actuation by causing the activation of lever 138 only at predetermined times. As a further alternative, the safety assembly may be provided with a wireless receiver for causing activation of the lever 138 upon receipt of an externally generated signal. Hence, the safety assembly 130 may take actuation control of the device 110 out of the hands of the patient and place such control into an actuation limiting timer or in the hands of a person more qualified than the patient to oversee the delivery of the insulin.

Figure 11:
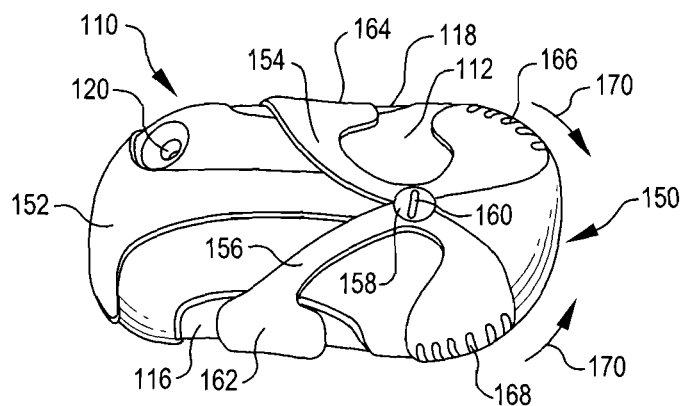
FIG. 11 is a perspective view of another infusion device and joined safety assembly according to still further aspects of the present invention.

FIG. 11 shows a still further embodiment. Here, it may be seen that another safety assembly 150 is snapped onto the enclosure 112 of the device 110. The safety assembly 150 includes a frame 152 arranged to lockingly engage the enclosure 112 of the device 110. The frame 152 carries crossing arms 154 and 156. The arms 154 and 156 intersect at a pivot point including a lock 158. When the lock 158 is unlocked by a key (not shown) inserted into a slot 160 of lock 158, the arms 154 and 156 are free to pivot with respect to each other. As may be noted, arm 156 has a pad 162 covering actuator button 116 and arm 154 has a pad 164 covering actuator button 118. Hence, when the lock 158 is locked, the arms 154 and 156 may not be moved relative to each other to and the pads 162 and 164 will preclude actuation access to the actuating buttons 116 and 118. When the lock 158 is unlocked by qualified personnel, however, relative movement of the arms 154 and 156 is permitted allowing the actuator buttons to be actuated by the pressing of the pads 162 and 164, or by the pushing of the ends 166 and 168 of arms 156 and 154 towards each other as indicated by arrows 170.

Figure 12:
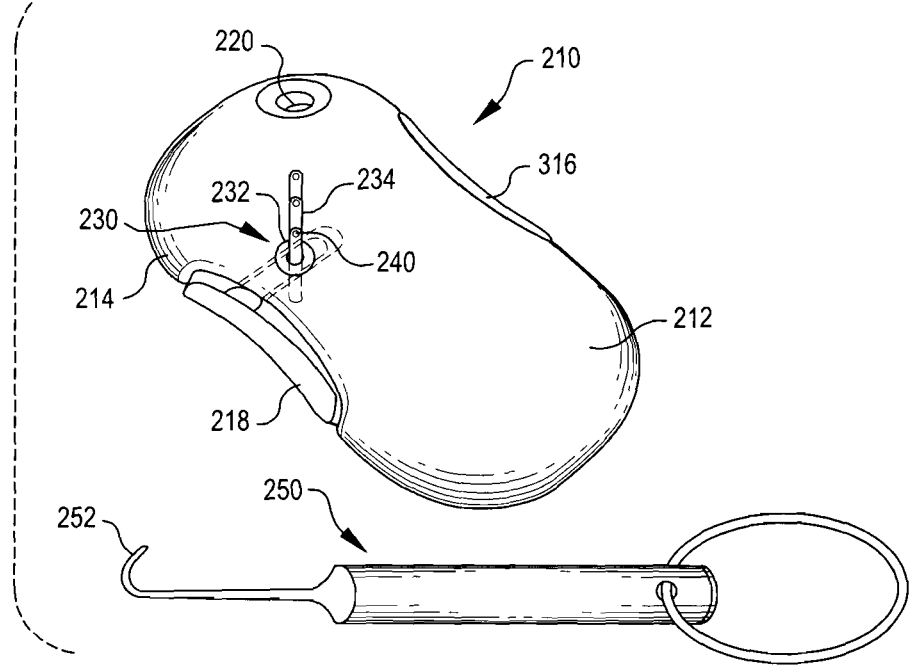
FIG. 12 is a perspective view of another infusion device and an internal safety assembly that disables actuator engagement of the device according to aspects of the present invention and a key for removing a pin element from and disabling the safety assembly.
Figure 13:
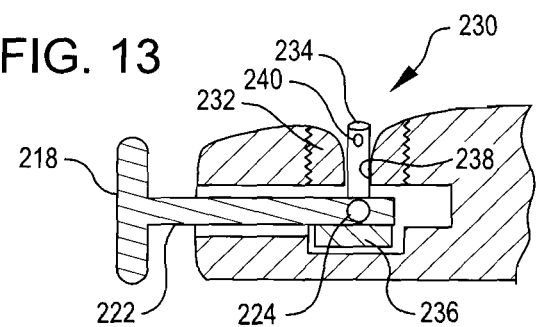
FIG. 13 is a partial sectional view illustrating details of the safety assembly of FIG. 12.

Referring now to FIGS. 12 and 13, they show another infusion device 210 and an internal safety assembly 230 that disables actuator engagement of the device according to further aspects of the present invention. Also shown is a key 250 for disabling the safety assembly 230 and permitting device actuation.

As in previous embodiments, the device 210 generally includes an enclosure 212, a base 214, a first actuator button 216, a second actuator button 218, and a fill port 220. The device 210 preferably includes the actuation mechanism previously described requiring concurrent actuation of the actuator buttons 216 and 218 to actuate the device 210 and deliver a dose of insulin.

With respect to the safety assembly 230, it generally includes an insert 232, a locking pin 234, and a magnet 236. The insert 232 is threaded into the device and has a center bore 238 dimensioned for receiving the locking pin 234. The actuator button 218 includes a shaft 222. The shaft has an aperture 224, also dimensioned to receive the locking pin 234. As thus may be seen in FIG. 13, when disabling actuation of the device 210, the locking pin extends through the bore 238 and the aperture 224 to preclude translation of the shaft 222 and thus actuation of the actuator button 218. The locking pin 234 is releasably held in place by the magnet 236.

As may be further noted in FIGS. 12 and 13, the locking pin 234 has a hole 240. The hole 240 permits the locking pin 234 to be engaged by the pointed end 252 of the key 250. This allows the locking pin 234 to be removed from the aperture 224 and bore 238 to free the shaft 222 for linear translation and depression of the actuator button 218. The actuator button may then be depressed concurrently with actuator button 216 to cause a dose of insulin to be delivered to the patient. After dosage delivery, the locking pin 234 may be returned to the bore 238 whereupon it will be pulled by magnet 236 down into its blocking location in the aperture 224 to once again preclude unintended actuation of the device 210. Complete removal of the pin from the device may be prevented by a collar or other attachment (not illustrated) to prevent loss of the pin.

As may be appreciated from the forgoing, the safety assembly 230 precludes unintended actuation of the device 210. Here, the safety assembly 230 does not preclude unintended actuation of the device 210 by precluding access to the actuator buttons as in precious embodiments, but by disabling actuator engagement of the device instead. Further, such actuation disablement may be achieved by precluding depression of one or more of the actuator buttons 218 and 216.

Figure 14:
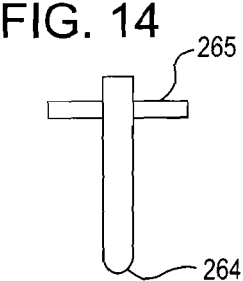
FIG. 14 is a side view of an alternative pin that may be employed in the safety assembly of FIG. 12.
Figure 15:
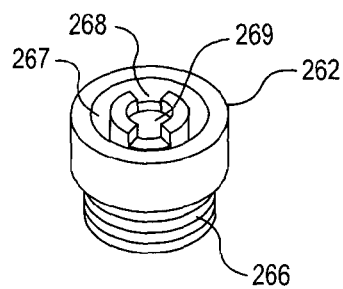
FIG. 15 is a perspective view of an insert arranged to receive the pin FIG. 14.
Figure 16:
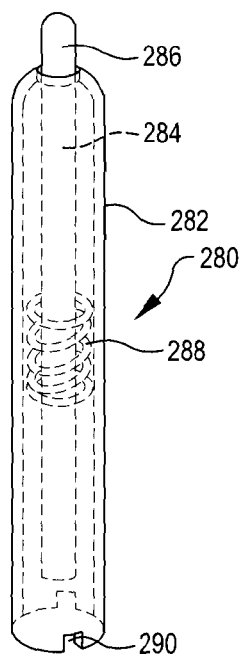
FIG. 16 is a perspective view of a key which may be employed to remove the pin of FIG. 14 for disabling its safety assembly.

FIGS. 14-16 show an alternative locking pin 264, insert 262, and key 280 for use in the embodiment of FIGS. 12 and 13. The insert 262 includes external threads 266 to permit the insert 262 to be threaded into the device 210 in place of insert 232. The insert 262 has a bore 268 for receiving the pin 264. The pin 264 includes a cross member 265 arranged to seat inside of a notch 269 of the insert 262 that is transverse to the bore 268.

The key 280 includes a cylindrical housing 282 and a magnetic pin 284 therein. The magnetic pin 284 has an end portion that extends beyond the end of the housing 282. A spring 288 is arranged within the housing 282 to bias the magnetic pin 284 in the position shown. The other end of the housing includes a notch 290 to capture the cross member 265 when the key 280 is inserted into an annular recess 267 of the insert 262.

When it is desired to activate the device, the key 280 is place into the annular recess 267 of the insert 262 with the notch 269 surrounding the cross member 265 of the locking pin. The end 286 of the magnetic pin 284 may now be pressed to cause the magnet pin 284 to attract and capture the locking pin 264. The key 280 may now be separated from the insert 262, drawing the locking pin 264 with it. The actuator button 218 is now free to be depressed and actuated concurrently with the other actuator button 216 to cause a dose of insulin to be delivered. After the dose is delivered, the key 280 with the locking pin 264 attached thereto by magnetic attraction may be rejoined with the insert to return the cross member 265 to within the notch 269. The magnetic pin 284 may now be disengaged to return to the position shown in FIG. 16. This separates the key 280 from the pin which is once again disposed within the bore 268 to once again disable actuator engagement.

Figure 17:
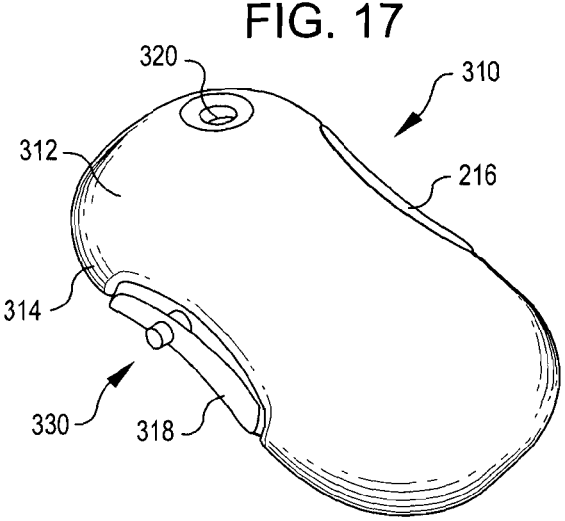
FIG. 17 is a perspective view of another infusion device and including a safety assembly that disables actuator engagement of the device according to further aspects of the present invention.
Figure 18:
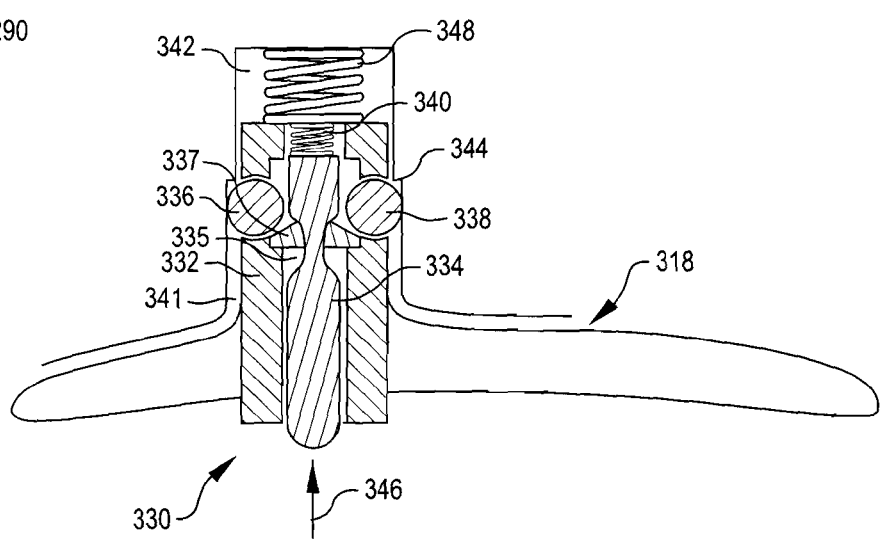
FIG. 18 is a partial sectional view illustrating details of the safety assembly of FIG. 17.

Referring now to FIGS. 17 and 18, they show another infusion device 310 including a safety assembly 330 that disables actuator engagement of the device according to further aspects of the present invention. As in previous embodiments, the device 310 generally includes an enclosure 312, a base 314, a first actuator button 316, a second actuator button 318, and a fill port 320. The device 210 preferably includes the actuation mechanism previously described requiring concurrent actuation of the actuator buttons 216 and 218 to actuate the device 210 and deliver a dose of insulin.

The actuator 318 includes a cylindrical extension 332. The safety assembly 330 includes a locking pin 334, a pair of spheres 336 and 338, and a spring 340. The cylindrical extension 332 is arranged to translate within a generally cylindrical bore 341. The bore 341 has a reduced diameter portion 342 dimensioned to receive the cylindrical extension 332 and forming an annular shoulder. The pin 334 includes a circumferential groove 335 and carries an annular resilient disk 337 within the groove 335.

As shown in FIG. 18, the safety assembly 330 is arranged to disable actuator engagement of the actuator button 318. An attempt to depress the actuator button 318 fails because the spheres 336 and 338 engage the shoulder 344. When delivery of a dose of insulin is desired, the pin 334 is pushed inward an indicated by arrow 346, The groove 335 will align with the spheres 336 and 338. The spheres 336 and 338 are now free to move into the groove 335 to clear the shoulder 344. The cylindrical extension 332 may now translate to permit the actuator button 318 to be depressed. After the actuator button 318 is depressed, the actuator button 318 and cylindrical extension 332 are returned to their initial positions by a spring 348. During the return of the actuator button 318 and the cylindrical extension 332, the resilient disk 337 will push the spheres 336 and 338 outwardly to once again engage the shoulder 344. The safety assembly 330 is again configured to disable actuator engagement.

Still further in accordance with this embodiment, the actuator button 318 may be removed from the device between doses. Hence, the actuator button may also serve as a key to be held by a responsible party who administers the dosage.

Figure 19:
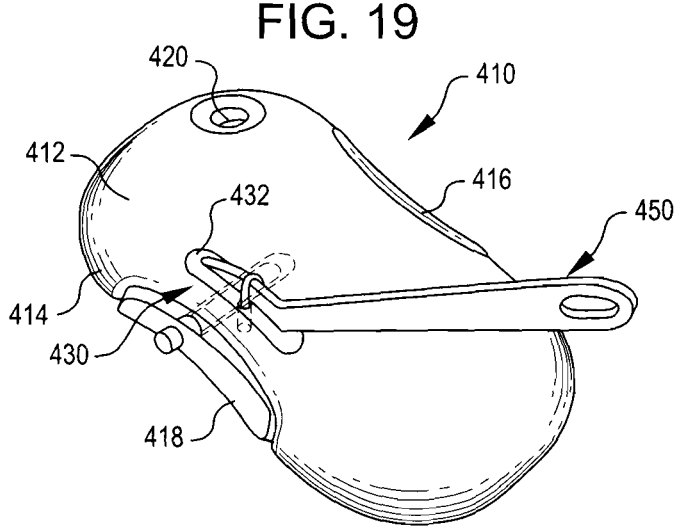
FIG. 19 is a perspective view of another infusion device having a safety assembly that disables actuator engagement of the device according to additional aspects of the present invention and a key for removing a pin element from and disabling the safety assembly.
Figure 20:
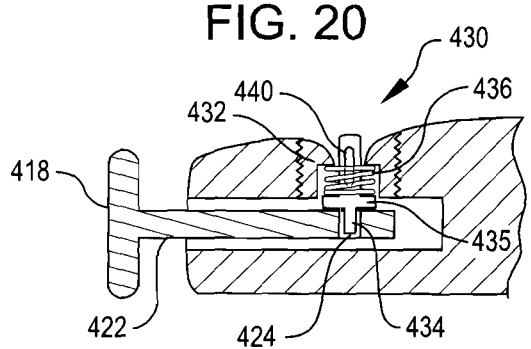
FIG. 20 is a partial sectional view illustrating details of the safety assembly of FIG. 19.

Referring now to FIGS. 19 and 20, they show another infusion device 410 and an internal safety assembly 430 that disables actuator engagement of the device according to further aspects of the present invention. Also shown is a key 450 for disabling the safety assembly 430 and permitting device actuation.

As in previous embodiments, the device 410 generally includes an enclosure 412, a base 414, a first actuator button 416, a second actuator button 418, and a fill port 420. The device 410 preferably includes the actuation mechanism previously described requiring concurrent actuation of the actuator buttons 416 and 418 to actuate the device 410 and deliver a dose of insulin.

With respect to the safety assembly 430, it generally includes an insert 432, a locking pin 434, and a spring 436. The spring 436 engages an annular flange 435 of the locking pin 434 to urge the locking pin 434 into a position that interferes with actuation of the actuator button 418. To that end, the actuator button 418 includes a shaft 422. The shaft has an aperture 424 dimensioned to receive the locking pin 434. The spring 436 thus urges the locking pin 434 into the aperture 424 to preclude the actuator button 418 from being depressed.

As may be further noted in FIGS. 19 and 20, the locking pin 434 has a slot 440. The slot 440 is dimensioned to receive the distal end of the key 450 as illustratred in FIG. 19. The key 450, when pivoted, causes the locking pin 434 to be pulled from the aperture 424 to free the shaft 422 for linear translation and depression of the actuator button 418. The actuator button may them be depressed concurrently with actuator button 416 to cause a dose of insulin to be delivered to the patient. After dosage delivery, the key 450 is pivoted back along with the pulling of the spring 436 to return the locking pin 434 to the aperture 224 to once again preclude unintended actuation of the device 410.

Figure 21:
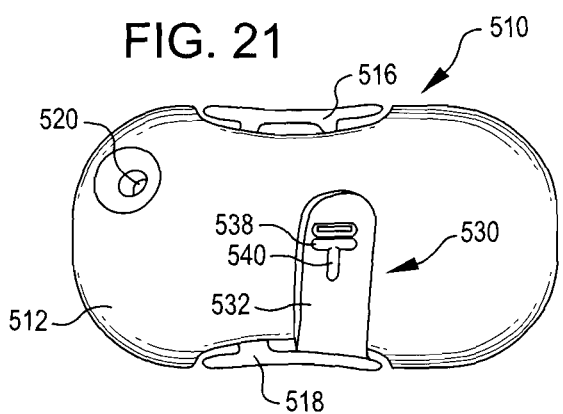
FIG. 21 is a top view of another infusion device and an attachable safety assembly that disables actuator engagement of the device according to still further aspects of the present invention.
Figure 22:
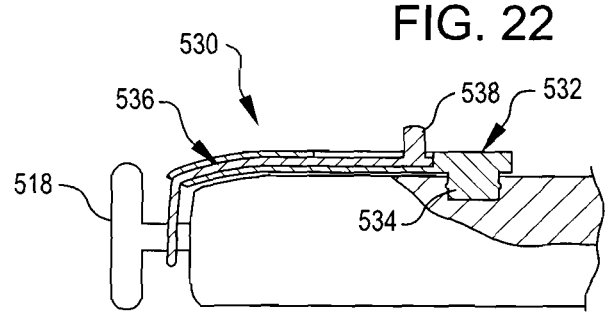
FIG. 22 is a partial sectional view illustrating details of the safety assembly of FIG. 21.

FIGS. 21 and 22 show an embodiment where the safety assembly is arranged to disable actuator engagement and is arranged to be attached to the enclosure of the device. More specifically, FIG. 21 shows an infusion device 510 that generally includes an enclosure 512, a base 514, a first actuator button 516, a second actuator button 518, and a fill port 520. The device 510 preferably includes the actuation mechanism previously described requiring concurrent actuation of the actuator buttons 516 and 518 to actuate the device 510 and deliver a dose of insulin.

The safety assembly 530 defines a guide sheath that may be snap fitted to the enclosure 512 with a snap mechanism 534. A sliding member 536 is arranged to slide within the sheath 532 between a position blocking depression of actuator button 518. The sliding member 536 carries a knob 538 that extends through an elongated slot 540 of the sheath 536. Grasping the knob 538 and moving it allows the sliding member 536 to be displaced from a first position blocking depression of the actuator button 518 to a second position clear of the actuator button 518 to permit it to be depressed.

Figure 23:
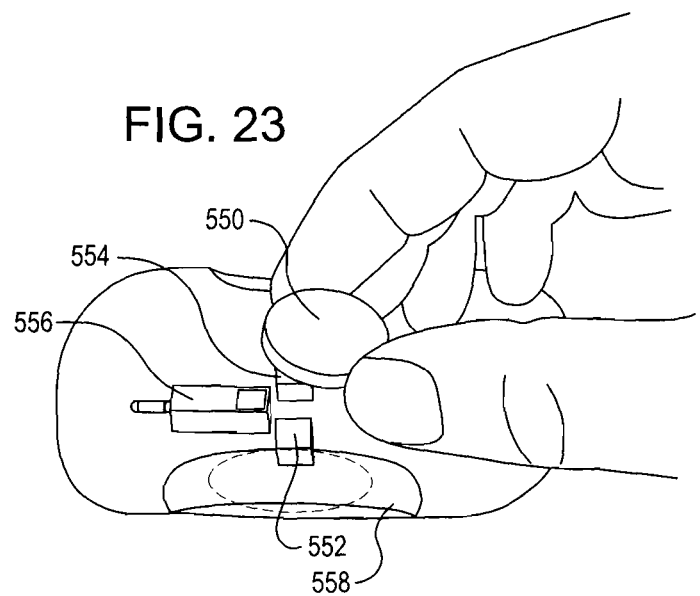
FIG. 23 is a perspective view showing another infusion device having an actuator safety assembly being enabled with an external magnet.

FIG. 23 shows another infusion device having an actuator safety assembly in the process of being enabled with an external magnet. Here, a magnet 550 is employed to complete an operative connection between actuator shaft portions 552 and 554. More particularly, an actuator button 558 has a first shaft portion 552, a center shaft portion 556, and a final shaft portion 554. There is a gap 557 between the first and final shaft portions 552 and 554 that is wide enough that fully depressing activator 570 fails to move first shaft portion 552 far enough to contact final shaft portion 554. Therefore, depressing actuator button 558 as no effect unless the center shaft portion 556 is brought into aligned engagement relation with the shaft portions 553 and 554. Hence, when a dose of insulin is desired, the magnet 550 is first brought into magnet engagement of the center shaft portion 556 to cause the center shaft portion to be drawn into aligned engagement relation with shaft portion 552 and 554. The actuator button 558 may now be depressed to successfully deliver a dose of insulin.

Figure 24:
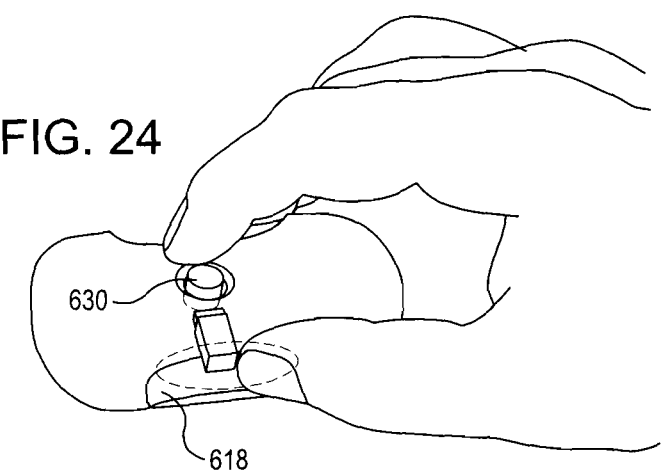
FIG. 24 is a perspective view showing another infusion device having an actuator safety assembly being disabled by the engagement of a dexterity button according to further aspects of the present invention.
Figure 25:
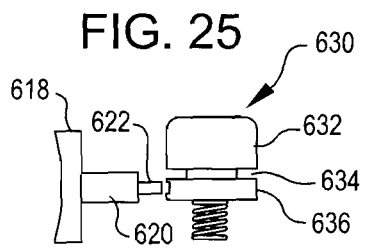
FIG. 25 is a side view illustrating details of the dexterity button of FIG. 24.

FIGS. 24 and 25 show a still further embodiment where a dexterity button 630 must first be successfully pushed before the actuator button 618 may be depressed. More specifically, as best seen in FIG. 25, The dexterity button includes a top portion 632, a bottom portion 636, and an annular space 634 there between. The dexterity button 630 is arranged to coact with the actuator button 618 that includes a shaft portion 620 and a narrow extension 622. The actuator button 619 cannot be depressed until the narrow extension 622 is aligned with the annular space and pushed therein. As the narrow extension 622 enters the annular space 634, the device is actuated to deliver the dose of insulin. Hence, the difficulty in manipulating the dexterity button 630 to align the narrow extension 622 with the annular space 634 serves to protect the device from being actuated unintentionally or accidentally.

While particular embodiments of the present invention have been shown and described, modifications may be made. For example, instead of manual actuation and spring loaded return of the valves used herein, constructions are possible which perform in a reversed manner by being spring actuated and manually returned. It is therefore intended in the appended claims to cover all such changes and modifications which fall within the true spirit and scope of the invention as defined by those claims.

What is claimed is:

1. A wearable infusion device comprising:
  a liquid medicament dispenser having an enclosure, a base attachable to a patient's skin and an actuator that, when enabled, causes a dose of the liquid medicament to flow to beneath the skin of the patient, the dispenser being arranged to provide a plurality of doses of the liquid medicament while being attached to the patient's skin; and
  a safety assembly arranged to preclude the actuator from being enabled, the safety assembly being releasable to permit the actuator to be enabled for delivering a dose of the liquid medicament and resettable after the delivery of each dose of the liquid medicament to preclude the actuator from being enabled between dose deliveries, the safety assembly being releasable and resettable while the device is attached to the patient's skin.

2. The device of claim 1 wherein the actuator includes at least one control button which when depressed, enables the actuator and wherein the safety assembly comprises a moveable cover that overlies the at least one control button when precluding the actuator from being enabled and moveable to expose the at least one control button to permit the actuator to be enabled.

3. The device of claim 2, further comprising a frame attachable to the dispenser enclosure, wherein the moveable cover is mounted for sliding movement on the frame.

4. The device of claim 1 wherein the safety assembly includes an activation lever and a drive member.

5. The device of claim 1, wherein the safety assembly comprises a lock mechanism.

6. The device of claim 1 wherein the safety assembly includes a locking pin arranged to reversibly interfere with the actuator.

7. The device of claim 6, wherein the safety assembly further includes an urging member that urges the locking pin into an interfering position to interfere with the depression of the actuator.

8. The device of claim 7, wherein the locking pin is further arranged for temporary release from the interfering position against the urging of the urging member.

9. The device of claim 1, wherein the safety assembly is arranged to preclude access to the actuator.

10. The device of claim 1, wherein the safety assembly is arranged to disable actuator enablement.

\* \* \* \* \*